United States Patent [19]

Ligtenberg et al.

[11] Patent Number: 4,589,970
[45] Date of Patent: May 20, 1986

[54] APPARATUS FOR SELECTIVELY MEASURING IONS IN A LIQUID

[75] Inventors: Hendrikus C. G. Ligtenberg, Nietap; Albertus Veld, Roden, both of Netherlands

[73] Assignee: Cordis Europa N.V., Roden, Netherlands

[21] Appl. No.: 641,911

[22] Filed: Aug. 16, 1984

[30] Foreign Application Priority Data

Aug. 24, 1983 [NL] Netherlands ............... 8302963

[51] Int. Cl.⁴ ............................................. G01N 27/30
[52] U.S. Cl. ..................................... 204/406; 204/412; 204/416; 357/23.13; 357/25
[58] Field of Search ................. 204/416, 406, 412; 357/25, 23.13

[56] References Cited

U.S. PATENT DOCUMENTS

| 4,020,830 | 5/1977 | Johnson et al. | 128/2 E |
| 4,086,642 | 4/1978 | Yoshida et al. | 361/91 |
| 4,397,714 | 8/1983 | Janata et al. | 204/1 T |
| 4,411,741 | 10/1983 | Janata | 204/1 T |
| 4,514,646 | 4/1985 | Ando et al. | 357/23.13 X |

FOREIGN PATENT DOCUMENTS

| 0043284 | 1/1982 | European Pat. Off. | 357/23.13 |
| 140881 | 1/1979 | Japan | 357/23.13 |
| 2060255A | 4/1981 | United Kingdom . | |

OTHER PUBLICATIONS

Rosemary Smith et al., Sensors and Actuators, 5, pp. 127–136, (1984).
Thesis of Rosemary Smith entitled: "Ion-Sensitive Field Effect Transistors with Polysilicon Gates", Department of Engineering, The University of Utah, Jun. 1982.

Primary Examiner—G. L. Kaplan
Attorney, Agent, or Firm—Thomas R. Vigil; Henry W. Collins

[57] ABSTRACT

The apparatus (14) is constructed and arranged to measure ions in a liquid (30) and comprises a measuring circuit (10) including an ISFET (16), a reference electrode (32), an amplifier (22) and a protection system (12)/guard circuit (40) connected to the measuring circuit (10). The protection system 12/guard circuit 40 comprises at least one electrode (46 or 47) connected via a low-impedance contact (or ring 62/46 or ring electrode 42) to the liquid (30) and coupled to the ISFET (16) by a protective element (64; 65, 66; or 68 and/or 50; 51, 52; 54; 56; or 58) having a low-impedance for high voltages and a high resistance to low voltages.

In one preferred embodiment, the ISFET (16) is provided on a chip (90) and has an electrode (46/62) in as closely spaced relationship as possible to the gate region (34) of the ISFET (16).

14 Claims, 6 Drawing Figures

APPARATUS FOR SELECTIVELY MEASURING IONS IN A LIQUID

BACKGROUND OF THE INVENTION

1. Field of the Invention

The present invention relates to an apparatus for selectively measuring ions in a liquid and more specifically to a protection system for protecting an ion sensor of the apparatus. The apparatus comprises a measuring circuit including a chemically selective ion sensor in the form of an ion-sensitive field effect transistor (ISFET), a reference electrode, and an amplifier.

1. Description of the Prior Art

Measuring apparatus for measuring ions in a liquid using an ISFET has been previously proposed. See for example the Johnson et al. U.S. Pat. No. 4,020,830. Such an apparatus includes a measuring circuit and an ISFET immersed in a liquid for selectively measuring the ion activity in the liquid. Different ISFETs are used for measuring different ion activities, such as, for example, pH, pK and pNa.

Although the use of an ISFET in such a measuring apparatus has been found to be very useful for measuring ions, especially in the medical and biomedical field, such usefulness has some limitations in actual practice. In this respect, voltages that develop between the surface of the gate insulator of the ISFET and the underlying bulk material of the ISFET establish an electrical field in the gate insulator which may adversely affect the operation of the ISFET.

If this electrical field, which may be caused by external influences, exceeds a maximum value, dielectriccal breakdown may occur in the gate insulator region and the ISFET may be damaged. When the gate insulator consists of a multilayer system (for example of combinations of $SiO_2$—$Si_3N_4$ or $SiO_2$—$Al_2O_3$), an unduly strong electrical field may produce still another effect, namely a shift in the threshold voltage of the ISFET, which may be permanent or which is only corrected after a long period of time. This results in the apparatus being permanently or temporarily out of order since the calibration of the apparatus is now incorrect.

Accordingly, it is desirable to provide some form of protection structure or circuitry to prevent the establishment of such electrical field or to prevent the calibration of the apparatus from being disturbed or upset by the electrical field. In this respect, an electrical field may be created by external influences or effects such as, for example, from electrosurgical apparatus, heart defibrillation apparatus, electromagnetic influences resulting from switching inductive elements on or off, and also from electrostatic voltages generated during the manufacture of the ISFET sensor or during use of the apparatus in practice.

It has heretofore been proposed to take steps to protect ISFET sensors from damage due to the presence of high voltages. See for example the Thesis of Rosemary Smith entitled "Ion Sensitive F.E.T. with Polysilicon Gates" at the University of Utah, June, 1982. This publication proposes the application to the gate insulator of a conductive polysilicon layer which, via a Zener diode or a MOSFET switch is connected to the source electrode of the ISFET. The polysilicon layer should in turn be provided with an ion sensitive layer of material to be contacted with the liquid to be investigated. It has been found, however, that the proposed protection system limits the application of the sensor to situations where only fast changes in ion activity are to be monitored.

It has also been proposed to provide a protection circuit for a metal-oxide semi-conductor field effect transistor (MOSFET) which includes a MOSFET. See the Yoshida et al. U.S. Pat. No. 4,086,642.

Further, it has been proposed to provide a silicon, PN junction surge current suppressor for protecting electronic circuitry. See U.K. patent application No. 2060255.

ISFETS, however, have no metallic gate electrode, in a way similar to a MOSFET, to which a protective element can be connected.

SUMMARY OF THE INVENTION

The measuring apparatus of the present invention includes a protection system constructed and arranged and connected to substantially fully cancel or neutralize the external influences or effect, or their affect, on a measuring apparatus including an ISFET without the protection system having an adverse affect on the behavior of the ISFET sensor under normal operating conditions.

According to the invention, there is provided an apparatus for selectively measuring ions in a liquid, said apparatus comprising a measuring circuit including a chemically sensitive ion sensor in the form of an ion sensitive field effect transistor (ISFET), a reference electrode, and an amplifier, characterized in that said apparatus includes a protection system for the ISFET comprising a low impedance contact, a protective element, and at least one electrode connectable to the liquid via the low-impedance contact to the liquid and coupled to said ISFET by the protective element which has a low impedance to high voltages above the operative voltage range of said ISFET and a high resistance to low voltages below the operative voltage range of said ISFET and which is capable of becoming operative outside the operative range of said ISFET.

Further, according to the invention, there is provided an ISFET chip, characterized by having an electrode on the chip closely adjacent to the gate region of the ISFET.

DESCRIPTION OF THE PREFERRED EMBODIMENTS

Figure 1:
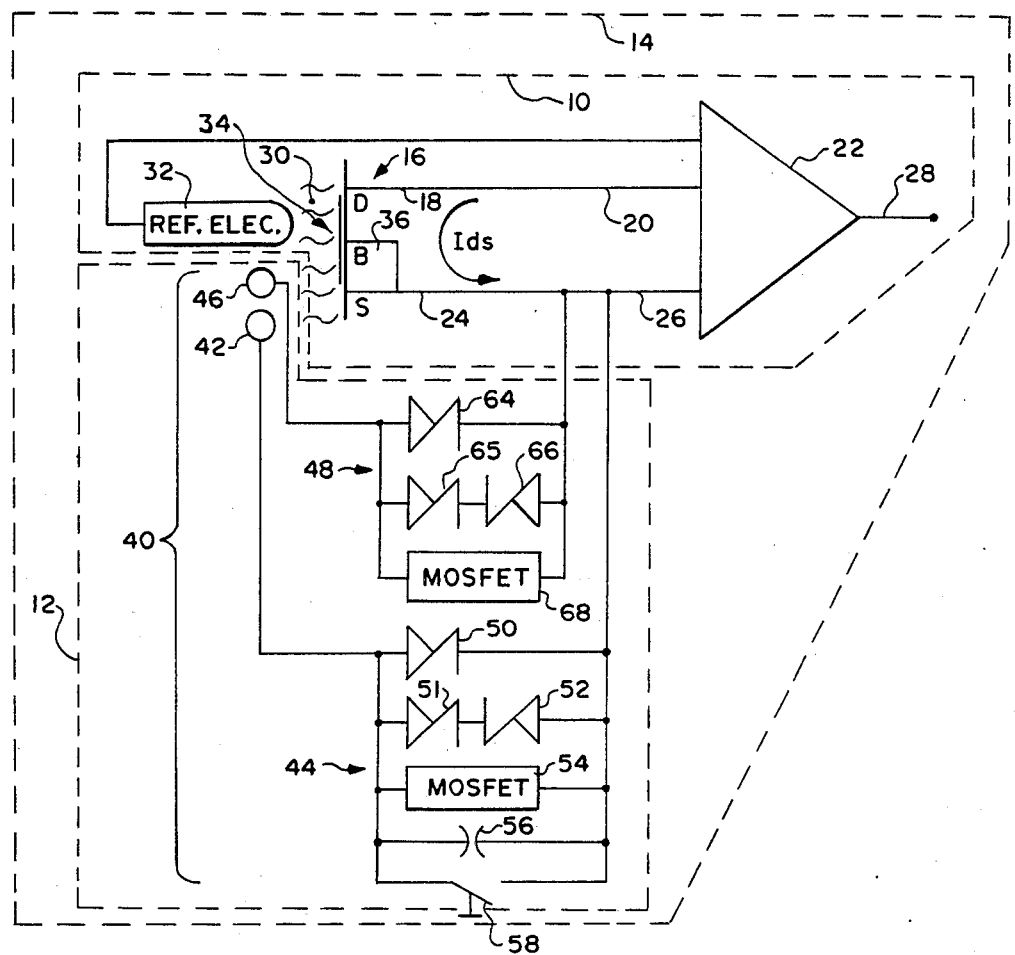
FIG. 1 is a schematic circuit diagram of circuitry for a measuring apparatus including a protection system constructed according to the teachings of the present invention for measuring ions in a liquid.

Referring now to the drawings in greater detail there is illustrated schematically in FIG. 1 a measuring circuit 10 including a protection system 12 for a measuring apparatus 14 (FIGS. 1, 2 and 3) constructed according to the teachings of the present invention.

The circuit 10 includes an ion-sensitive field effect transistor (ISFET or ISFET sensor) 16 having a drain 18 coupled to one input 20 of an amplifier 22 and a source 24 coupled to another input 26 of the amplifier 22 which has an output 28 that has an output signal indicative of the concentration of ions in a liquid (such as blood) 30.

Further, the circuit 10 includes a reference electrode 32 which applies a reference voltage to liquid 30 so that gate region 34 of the ISFET 16 is electrically connected to the amplifier 22, thus enabling control of the drain source current $I_{DS}$ of the ISFET 16 in a manner similar to that used with MOSFETs.

The voltage that is experienced by the ISFET 16 consists of a portion that is dependent on the ion activity in the liquid 30 to which the ISFET 16 is specifically sensitive, and of the externally applied voltage $V_{RB}$ (voltage between the reference electrode 32 and the bulk 36 of the ISFET 16). A change in ion concentration gives rise to a change in drain-source current. This change in drain-source current can be compensated for by adjusting the externally applied voltage $V_{RB}$. The relationship between ion activity and the developed voltage is known. Therefore it follows that from the correction of $V_{RB}$, the change in ion concentration can be calculated. The amplifier 22 measures the drain-source current constantly and corrects $V_{RB}$ for changes in that current in order to keep it constant. The output voltage of the amplifier 22 is proportional to the changes in $V_{RB}$, so that the signal at the output 28 of the amplifier 22 can be used as a measure of the concentration of ions in the liquid 30.

As shown in FIG. 1, the ISFET 16 also has a bulk contact 36.

In accordance with the teachings of the present invention, the protection system 12 includes a guard circuit 40 coupled between the source 24 and the liquid 30 and including a first electrode 42 coupled to the source 24 through a first protection circuit 44 and a second electrode 46 coupled to the source 24 through a second protection circuit 48, both having a high resistance to low voltages and a low impedance to high voltages.

According to the teachings of the present invention, the first electrode 42 is preferably made of a metal, for example, of stainless steel having good blood compatability, or of titanium. In other words, the first electrode 42 should be made of a conductive material having good blood compatibility and having a surface area sufficiently large to provide a low-impedance contact with the liquid 30 when the ISFET 16 and reference electrode 32 are immersed into the liquid 30 being investigated.

The first electrode 42 serves to protect the ISFET 16 from high A.C. voltages which occur, for example, with the use of an electrosurgical apparatus. For this purpose, the first electrode 42 is coupled to the source 24 by one or more protective elements in the protection circuit 44, such as by a diode 50, two bucking or reverse polarity series connected diodes 51, 52 and/or a MOSFET 54 which becomes conductive outside the operative range of the ISFET 16. For example, a Zener diode or an avalanche diode or a MOSFET having a high threshold voltage to the measuring circuit can be used. A capacitor 56 may be used with or may replace the diodes 51, 52 and/or the MOSFET 54.

Also, the first electrode 42 can be coupled to the source 24 by a mechanical switch 58 serving as a protective element.

The protective elements 50–58 can, of course, be coupled to any contact which is in a low-impedance connection with the source 24 of the ISFET 16, for example, the source 24, drain 18 or bulk contact 36.

The second electrode 46 may take the form of a current conducting fork, strip or ring, and preferably a ring 62 (FIG. 3) of a current conducting material, such as aluminum or polysilicon, applied around the gate region 34 of the ISFET 16 and coupled by one or more protective elements in protection circuit 48, such as by a diode 64, two bucking or reverse polarity series connected diodes 65, 66, and/or a MOSFET 68 which become conductive outside the operative range of the ISFET 16, for example, a Zener diode or an avalanche diode or a MOSFET having a high threshold voltage to the measuring circuit.

As shown, the second electrode 46 is as closely spaced to the gate region 34 of the ISFET 16 as possible.

The choice for a protective element according to the teachings of the present invention is based on the condition that any leakage current which may be present within the operative range of the ISFET 16 gives rise to a shift in the reference electrode potential equal to the product of leakage current and impedance. This shift contributes to the voltage that is experienced by the ISFET 16, and accordingly has a negative effect on the accuracy of the measurement, which becomes unacceptable if the leakage current comes to be in excess of an acceptable limit, for example, is more than 10 nA. Therefore, within the operative range of the ISFET 16, the D.C. currents which may pass through the protective elements should accordingly be kept below the acceptable limit.

The diodes 50, 51, 52, 64, 65, and 66 or MOSFETs 54, 68 which become conductive outside the operative range of the ISFET 16, to be used according to the teachings of the present invention, have a breakdown voltage lower than the voltage in which the damage causing effects occur. The second electrode 46, thus connected to the measuring circuit 10, provides protection of the ISFET sensor 16 from electrostatic voltages which may occur during manufacture of the sensor 16 or also during use thereof.

When the apparatus 14 is being used at the same time that electrosurgery is being utilized, it is possible that a pulsating direct current will flow through the circuit formed by the reference electrode 32, the liquid 30, electrode 46, the protective elements 64 and/or 68, the ISFET 16 and the amplifier 22 of the apparatus 14. This current will influence the reference electrode 32 potential and also lead to the occurrence of a Coulometric effect and accordingly, will affect the pH of the liquid 30 to be measured. This problem may be overcome by coupling the second electrode 46 into the circuit of the apparatus 14 with the two diodes 65, 66 connected in series with reverse polarity. The same approach is valid for protection circuit 44.

Figure 3:
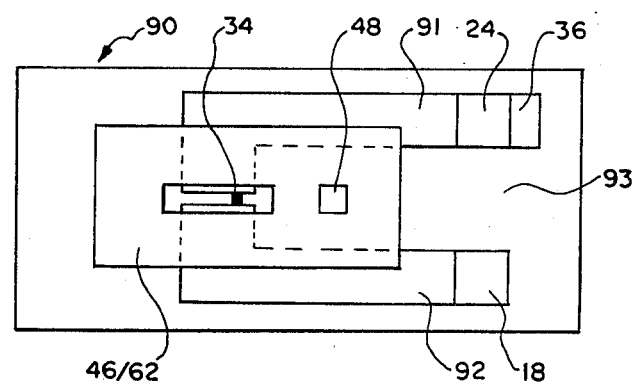
FIG. 3 is a plan view of an ISFET chip including a protection electrode particularly adapted for use in the measuring apparatus of the present invention.

Also, when the protective element is diode 64, MOSFET 68 and/or the diodes 65, 66, these elements can be used in combination for both the first and the second electrode and may be arranged on the ISFET chip (90—FIG. 3).

In the choice of a capacitor 56 it is important that the capacitance of the capacitor 56 is sufficiently high in order that the impedance may be low enough for the frequency of the spurious A.C. voltage applied, for example, that applied in electrosurgical operations. A capacitance of 100 nF or more is generally satisfactory for this purpose.

If desired, the capacitor 56 may be included in the amplifier 22.

When the mechanical switch 58 is used, it is effective to use a relay switch (not shown) for this purpose, which is activated by the source of interference and is maintained in the activated state for the time the interference lasts.

For example, in an apparatus 14 constructed according to the teachings of the present invention, the protection system 121 or guard circuit 40 can be constructed so that the first electroce 42 is connected to the capacitor 56 and the second electrode 46 is connected to the diode 64, the MOSFET 68 and/or the diodes 65, 66.

Figure 2:
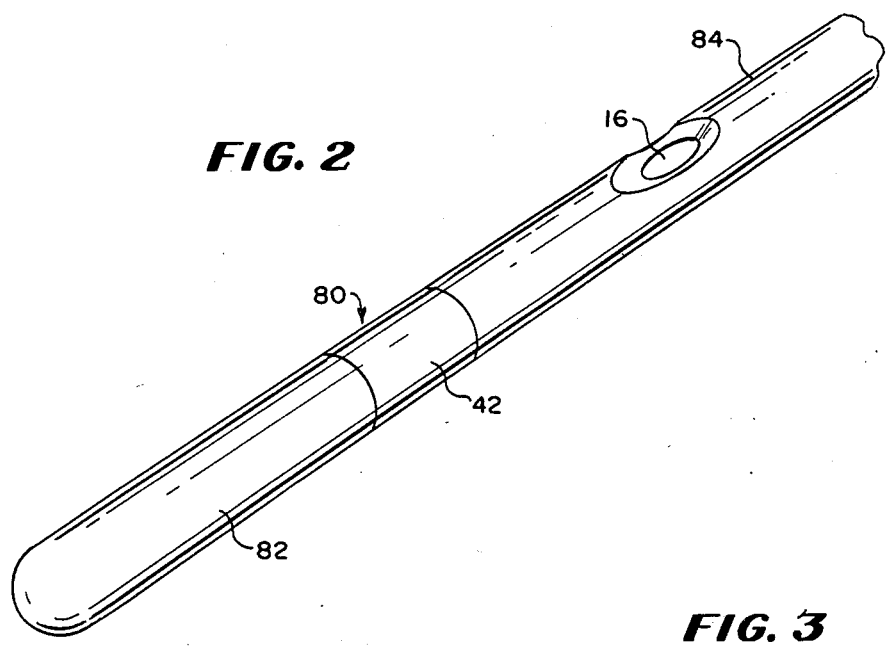
FIG. 2 is a perspective view of one embodiment of the measuring apparatus shown schematically in FIG. 1 including a catheter mounting an ISFET sensor.

As shown in FIG. 2, the apparatus 14 can be mounted in a catheter 80 where the reference electrode 32 is mounted in a terminal or tip part 82. The first electrode 42 is then realized by a metallic ring 42 spaced slightly rearwardly of the tip part 82. The ring electrode 42 has a surface area of about 1 cm$^2$ which provides a low-impedance contact with the liquid 30 (FIG. 1) in which the catheter 80 is to be immersed. The ring 42 can be electrically connected to a terminal on the ISFET chip (90—FIG. 3) through a polypropylene capacitor 56 having a capacitance of 100 nF, which in this case is included in the ISFET amplifier circuit. The ISFET sensor 16 is housed or mounted by an epoxy resin within a housing portion 84 of the catheter 80 located rearwardly of the ring electrode 42.

A plan view of a chip 90 containing the ISFET 16 which can be mounted in housing portion 80 of the catheter 80 is shown in FIG. 3. The chip 90 includes a source 91, and a drain 92 diffused in bulk 93 of the chip 90 and provided with source bulk contact elements 24, 36 and drain contact element 18. A protective electrode, i.e., the second electrode 46 is realized by an aluminum ring 62 which is electrically connected to protective circuit 48 which is diffused in the bulk 93 of the ISFET chip 90. The second electrode 46/aluminum ring 62 is applied around the gate region 34 on the chip 90.

Figure 4:
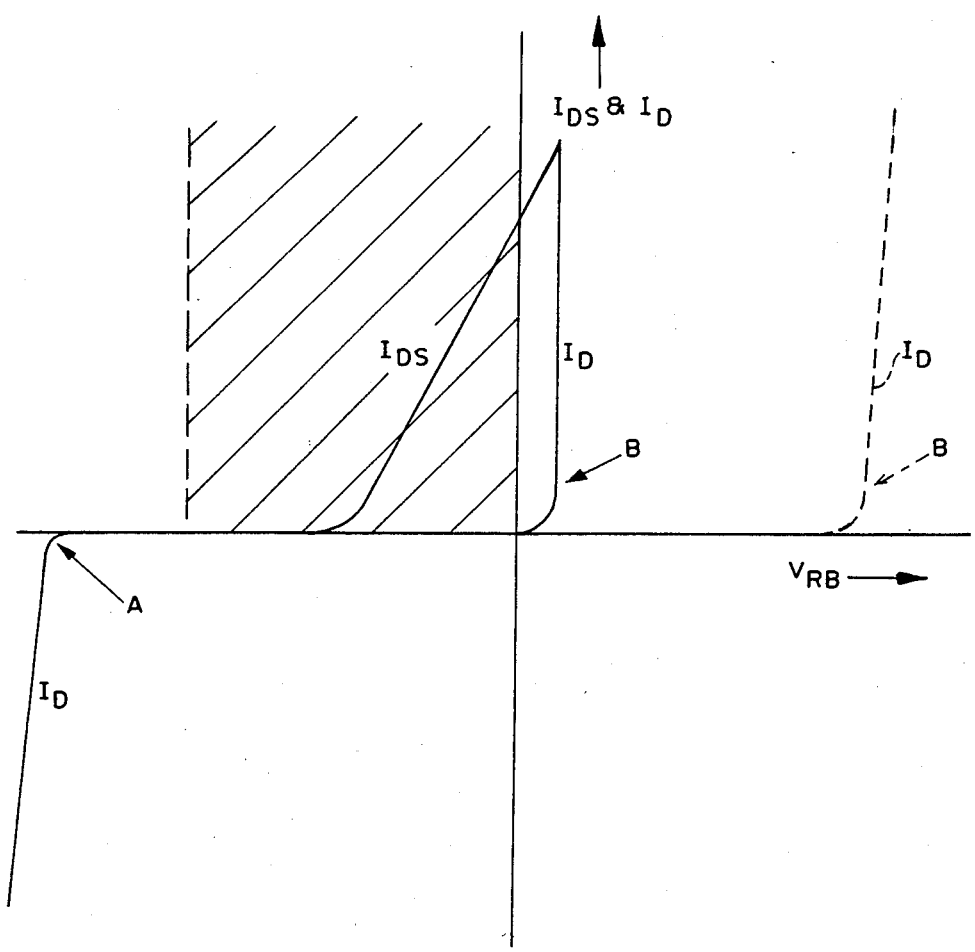
FIG. 4 is a graph of current versus voltage that shows the current to an ISFET and a protection diode when a diode is used in the protection system of the present invention.

In the graph shown in FIG. 4, the potential $V_{RB}$ of the reference electrode 32 relative to the bulk 36 of the ISFET 16 is plotted along the horizontal axis, and the current intensity along the vertical axis, with $I_D$ being the diode current and $I_{DS}$ being the drain source current. The hatched area in the graph represents the operative range of the ISFET sensor 16. The letter A designates the point of diode breakdown, and the letter B represents the diode pass characteristic.

Figure 5A:
FIGS. 5A and 5B are schematic circuit diagrams of the series connections of two diodes having reverse polarity to each other, which can be referred to as anti-series diodes and which can form part of the protection system of the present invention.
Figure 5B:
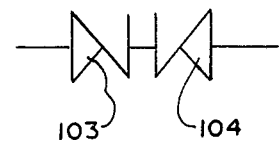

As stated above, the protective element can be a combination of two diodes (51, 52 or 65, 66) connected in anti-series or reverse polarity to each other. Such diodes may be two Zener diodes 101, 102 in a connection as represented in FIG. 5B. With such protective elements the graph of $I_D$ shown in FIG. 4 is modified to the graph of $I_D$ shown in phantom or dashed lines in FIG. 4.

The protection system or guard circuuit 40 constructed according to the teachings of the present invention offers adequate protection from external effects or influences resulting from electromagnetic sources of interference which may be encountered in the biomedical and industrial fields, for example, in cases in which the ISFET sensor 16 and apparatus 14 is used in cooperation with electrosurgical apparatus or heart defibrillation apparatus. The protection further extends to the danger of the occurrence of electrostatic voltages as may occur during the manufacture of the ISFET sensor 16 or also during use of the apparatus 14 in practice. Moreover, the protection offered by the guard circuit 40 according to the present invention is effective in combination with all types of housings of the ISFET sensor 16, for example, in the case of catheter tip sensors, flow cells, and other types of housings.

It will be understood that modifications can be made to the apparatus 14 and the ISFET chip 90 of the present invention, as described herein and shown in the accompanying drawings, without departing from the teachings or scope of the present invention. Accordingly, the scope of the present invention is only to be limited as necessitated by the accompanying claims.

I claim:

1. Apparatus for selectively measuring ions in a liquid, said apparatus comprising a measuring circuit including a chemically sensitive ion sensor in the form of an ion sensitive field effect transistor (ISFET), a reference electrode, and an amplifier, characterized in that said apparatus includes a protection system for said ISFET comprising a low-impedance contact, a protective element, and at least one electrode connectable to the liquid via said low-impedance contact and coupled to said ISFET by said protective element which has a low impedance to high voltages above the operative voltage range of said ISFET and a high resistance to low voltages below the operative voltage range of said ISFET and which is adapted to become operative outside the operative range of said ISFET.

2. The apparatus according to claim 1 characterized in that said protection system comprises a first electrode which, when said apparatus is immersed into the liquid to be investigated, has a low-impedance contact therewith, and a second electrode, spaced closely adjacent to the gate region of said ISFET, said two electrodes being each coupled via a corresponding protective element to a low-impedance contact for said ISFET.

3. The apparatus according to claim 2, characterized in that the first electrode is made of a conductive material and has a surface area sufficiently large to create a low-impedance contact with the liquid to be investigated when said apparatus is immersed into said liquid.

4. The apparatus according to claim 2, characterized in that said first electrode is coupled to said ISFET by a protective element comprising: a diode and/or a MOSFET which become conductive outside the operative range of the ISFET, or by a capacitor and/or a mechanical switch.

5. The apparatus according to claim 4, characterized in that said capacitor has a capacitance of about 100 nF or higher.

6. The apparatus according to claim 4 characterized in that said capacitor is included in the amplifier.

7. The apparatus according to claim 4, characterized in that said mechanical switch is a relay switch which is activated by a source of electromagnetic interference for the time of the duration of the interference.

8. The apparatus according to claim 4, characterized in that said first electrode is connected to said capacitor and said second electrode is connected to said diode and/or said MOSFET.

9. The apparatus according to claim 2 characterized in that said second electrode takes the form of a metallic ring around the gate region of the ISFET and is coupled to said ISFET via a diode and/or a MOSFET which forms said protective element and which becomes conductive outside the operative range of the ISFET.

10. The apparatus according to claim 9, characterized in that said second electrode is coupled to said ISFET via two diodes connected in anti-series (in reverse polarity to each other).

11. The apparatus according to claim 10, characterized in that the diode or diodes or the MOSFET are provided on the ISFET chip.

12. An IFSET chip characterized by having an exposed protective electrode on the chip closely adjacent to the gate region and by said electrode taking the form of a metallic ring positioned around the gate region of the ISFET.

13. An ISFET chip characterized by having an electrode on the chip closely adjacent to the gate region of the ISFET and by said electrode being coupled to said ISFET via a diode and/or MOSFET, arranged on the chip, which are adapted to become conductive outside the operative range of the ISFET.

14. The ISFET chip according to claim 13 characterized in that said electrode is coupled to said ISFET via two diodes connected in anti-series (in reverse polarity to each other).

* * * * *

UNITED STATES PATENT AND TRADEMARK OFFICE
CERTIFICATE OF CORRECTION

PATENT NO. : 4,589,970

DATED : May 20, 1986

INVENTOR(S) : HENDRIKUS C.G. LIGTENBERG et al.

It is certified that error appears in the above-identified patent and that said Letters Patent is hereby corrected as shown below:

Column 8, line 1 "IFSET" should be --ISFET--

Signed and Sealed this

Seventeenth Day of February, 1987

Attest:

DONALD J. QUIGG

Attesting Officer     Commissioner of Patents and Trademarks